(12) United States Patent
VanDusseldorp

(10) Patent No.: US 9,370,377 B2
(45) Date of Patent: Jun. 21, 2016

(54) EXTRACTION DEVICE

(75) Inventor: Gregg Alan VanDusseldorp, Valparaiso, IN (US)

(73) Assignee: endoMedical Concepts Inc., Fort Myers, FL (US)

( * ) Notice: Subject to any disclaimer, the term of this patent is extended or adjusted under 35 U.S.C. 154(b) by 0 days.

(21) Appl. No.: 13/115,691

(22) Filed: May 25, 2011

(65) Prior Publication Data

US 2011/0295266 A1    Dec. 1, 2011

Related U.S. Application Data

(60) Provisional application No. 61/348,377, filed on May 26, 2010.

(51) Int. Cl.
 *A61B 17/22* (2006.01)
 *A61B 18/24* (2006.01)

(52) U.S. Cl.
 CPC ......... *A61B 17/22031* (2013.01); *A61B 18/245* (2013.01); *A61B 2017/22035* (2013.01)

(58) Field of Classification Search
 CPC ................. A61B 17/22; A61B 17/221; A61B 2017/2215; A61B 17/22031
 USPC ......... 606/113, 114, 119–122, 124, 200, 127, 606/128, 138, 205–210, 142; D24/133, D24/143; D8/52, 54
 See application file for complete search history.

(56) References Cited

U.S. PATENT DOCUMENTS

| | | | |
|---|---|---|---|
| 835,688 A * | 11/1906 | Read | 606/122 |
| 4,174,715 A * | 11/1979 | Hasson | 606/206 |
| 5,281,230 A | 1/1994 | Heidmueller | |
| 5,944,728 A | 8/1999 | Bates | |
| 6,183,482 B1 * | 2/2001 | Bates et al. | 606/127 |
| 6,203,552 B1 | 3/2001 | Bagley et al. | |
| 6,416,519 B1 | 7/2002 | VanDusseldorp | |
| 6,500,182 B2 | 12/2002 | Foster | |
| 2002/0068954 A1 | 6/2002 | Foster | |
| 2004/0054377 A1 * | 3/2004 | Foster et al. | 606/167 |
| 2005/0222586 A1 * | 10/2005 | VanDusseldorp | 606/127 |

* cited by examiner

*Primary Examiner* — Ryan J Severson
*Assistant Examiner* — Anh Dang
(74) *Attorney, Agent, or Firm* — Hartman Global IP Law; Gary M. Hartman; Domenica N. S. Hartman

(57) ABSTRACT

Extraction devices adapted to grasp, hold and move a variety of biological materials. The extraction devices include a sheath with an interior passage and legs slidably received within the passage of the sheath. The legs are adapted to move outwardly away from each other when deployed from the sheath to establish a deployed position, and to move inwardly toward each other to collapse within the sheath and define a stowed position. Each leg has a transverse cross-sectional shape defined by a first surface that is concave and an oppositely-disposed second surface that is convex. The legs have adjacent distal ends that define a grasping and holding feature when the legs are moved between their deployed and stowed positions. Each distal end has an arcuate portion and defines a distal surface that is substantially parallel to the longitudinal axis of the corresponding leg thereof when the legs are in the stowed position. The concave inward surface of each leg and its distal surface cooperate to define at least two points adapted for grasping when the legs are retracted into the sheath.

20 Claims, 4 Drawing Sheets

EXTRACTION DEVICE

CROSS REFERENCE TO RELATED APPLICATIONS

This application claims the benefit of U.S. Provisional Application No. 61/348,377, filed May 26, 2010, the contents of which are incorporated herein by reference. In addition, this application is related to U.S. Pat. No. 6,416,519, dated Jul. 9, 2002. The contents of this patent are also incorporated herein by reference.

BACKGROUND OF THE INVENTION

The present invention generally relates to extraction devices capable of capturing and releasing hard objects, and particularly for surgically moving, manipulating and extracting biological material and man-made material from the human body, such as required in ureteroscopic and renal stone extraction procedures.

Various instruments are known in the art for surgically removing stones, calculi and other hard materials from the body. An example is an extraction instrument disclosed in U.S. Pat. No. 5,281,230 to Heidmueller as comprising a pair of bowls that are pivoted toward and away from each other by engaging their proximal ends with a sheath. Other types of extraction instruments make use of multiple wires that are flexed to grasp an object. For example, U.S. Pat. No. 5,944,728 to Bates discloses an instrument having arcuate wires with rectangular, round, D-shaped, or V-shaped cross-sections. The wires form a basket when a plunger associated with the instrument is in a distal position, allowing the legs to radially collapse toward each other. To expand the legs, the plunger must be actuated into engagement with the legs, forcing the legs radially apart from each other. As such, surgically moving, manipulating and extracting material from a body cavity is complicated by the requirement to additionally operate the plunger to expand and contract the legs.

Another example of an extraction instrument is disclosed in U.S. Pat. No. 6,203,552 to Bagley et al. As with Bates, the instrument taught by Bagley et al. has arcuate legs that form a collapsible basket when actuated with respect to a sheath. Each leg has a wedge-shaped cross-sectional shape, so that together they fill the cross-sectional area of the sheath. Contrary to Bates, the instrument disclosed by Bagley et al. does not require a separate plunger to expand (dilate) and collapse the basket.

U.S. Pat. No. 6,500,182 to Foster and U.S. Patent Application Publication No. 2002/00668954 to Foster disclose other extraction instruments configured to be actuated without the assistance of a plunger. Each instrument taught by Foster has resilient grasping members (legs) that form a basket or forceps when extended from a sheath, and which collapse toward each other when the sheath is advanced over the legs (or the legs are retracted into the sheath). According to Foster, the legs are formed by cutting or forming slots in an elongated cylindrical member, such as a cannula. If formed from a cannula, the legs are said to have semicircular cross-sectional shape. The edges of the legs are said to be spaced apart when in the compact (collapsed) position, a condition which appears to be inherent because each adjacent pair of legs is separated by the slot formed during the cutting/forming operation that defined the legs. As such, it appears the legs cannot be fully collapsed with the sheath, since the sheath cannot have an inner diameter smaller than the cannula from which the legs were defined and which must also be accommodated within the sheath.

There is an ongoing effort to devise surgical extraction instruments with greater grasping capabilities to more easily capture biological material during a variety of medical procedures.

BRIEF DESCRIPTION OF THE INVENTION

The present invention provides extraction devices adapted to grasp, hold and move a variety of biological materials.

According to one aspect of the invention, such an extraction device has a sheath with an interior passage and legs slidably received within the passage of the sheath. The legs are adapted to move outwardly away from each other when deployed from the sheath to establish a deployed position, and to move inwardly toward each other to collapse within the sheath and define a stowed position. Each leg has a transverse cross-sectional shape defined by a first surface that is concave and an oppositely-disposed second surface that is convex. The legs have adjacent distal ends that define a grasping and holding feature when the legs are moved between their deployed and stowed positions. Each distal end has an arcuate portion that extends along an arc of greater than 90 degrees, and each distal end defines a distal surface that is substantially parallel to the longitudinal axis of the corresponding leg thereof when the legs are in the stowed position. The concave inward surface of each leg and the distal surface cooperate to define at least two points adapted for grasping when the legs are retracted into the sheath.

Other aspects and advantages of this invention will be better appreciated from the following detailed description.

DETAILED DESCRIPTION OF THE INVENTION

Figure 1:
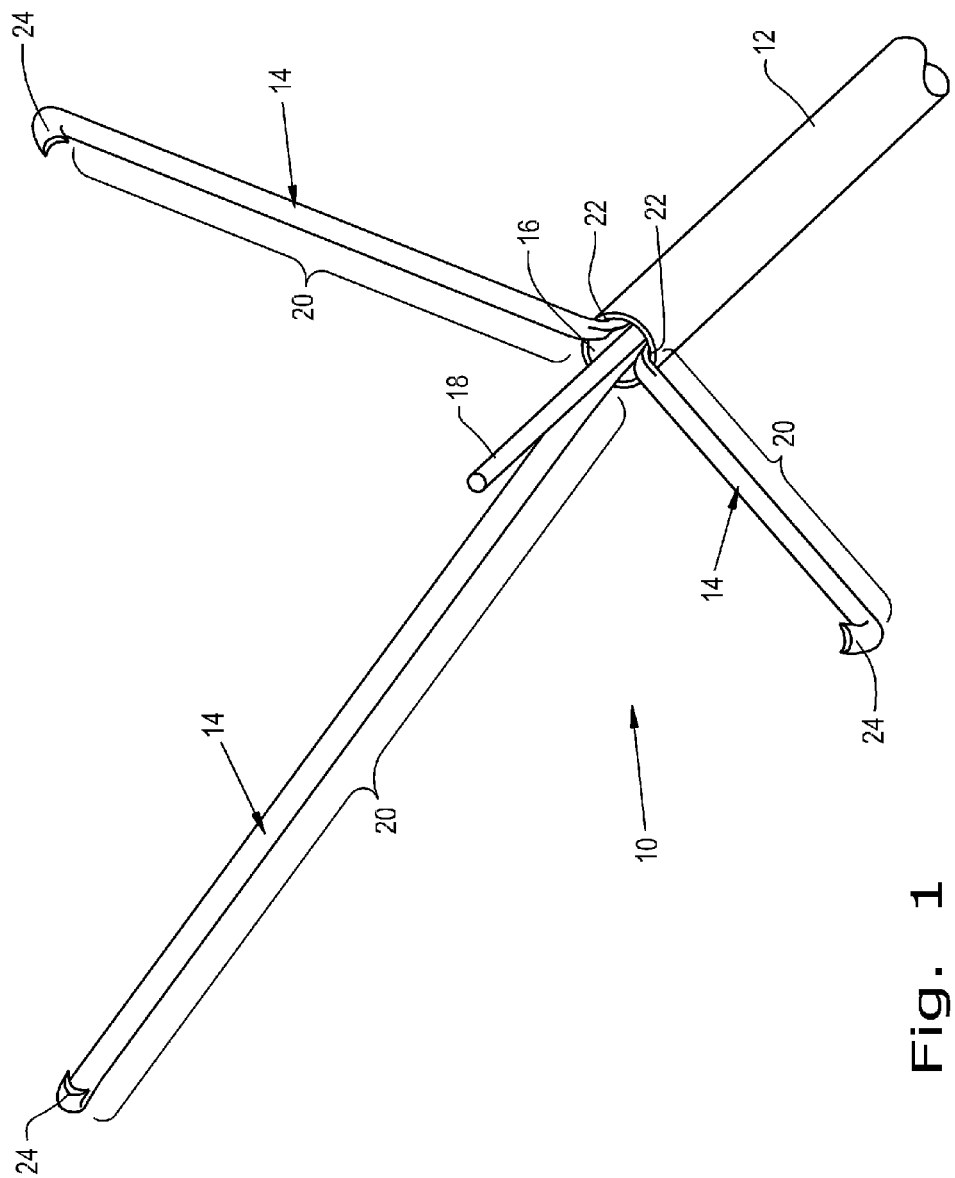
FIGS. 1 and 2 are perspective views of extraction devices in deployed positions in accordance with two embodiments of this invention.
Figure 2:
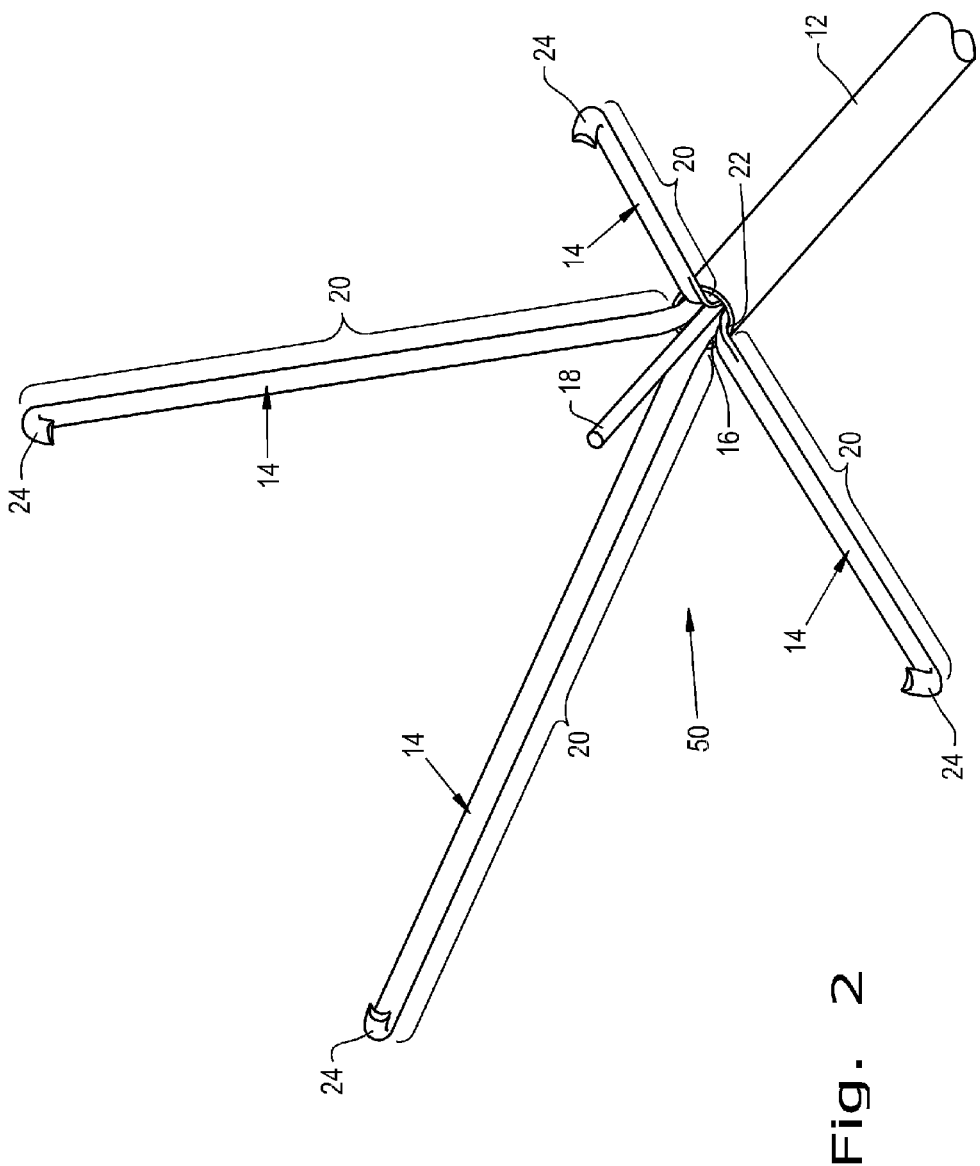

With reference to FIGS. 1 and 2, extraction devices 10 and 50 are shown in accordance two embodiments of the invention. The devices 10 and 50 are particularly intended and suitable for extraction procedures, in which biological materials are required to be surgically moved, manipulated and/or extracted from a cavity of the living body. As such, the devices 10 and 50 can be adapted for use as, for example, a urological, gynecological, cardiological, laparoscopical, or gastrointestinal instrument.

The extraction devices 10 and 50 are each depicted as comprising a sheath, 12 legs 14 that project from a passage 16 within the sheath 12, and a laser fiber 18 that also projects from the sheath passage 16. As known in the art, the legs 14 are adapted to capture and hold stones and other biological materials, and the laser fiber 18 can be employed to fragment the biological material. Alternatively or in addition, the sheath passage 16 may be sized to accommodate an irrigation or injection lumen. The legs 14 are shown as being deployed from the sheath 12 as a result of their distal portions 20 protruding from the sheath passage 16. The embodiments of FIGS. 1 and 2 differ primarily by having a different number of legs 14, namely, three and four legs 14, respectively, though embodiments having two legs 14 and more than four legs 14 are also within the scope of the invention. Unless otherwise noted, remarks directed to the device 10 or 50 of one of FIG. 1 or 2 will typically be applicable to the device 10 or 50 of the other figure.

Figure 6:
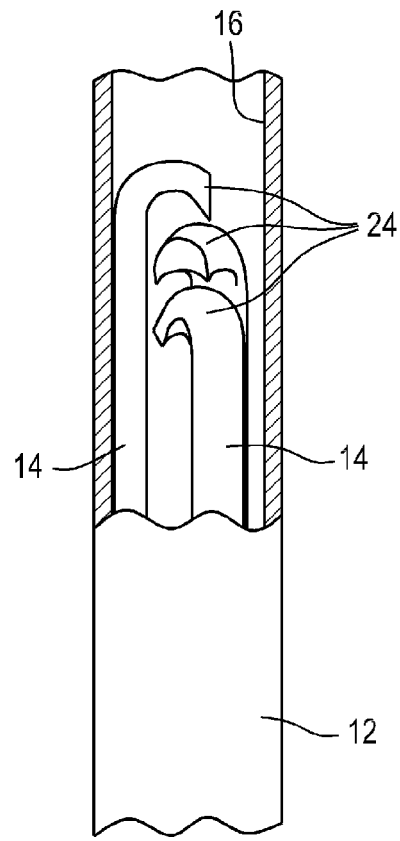
Figure 8:
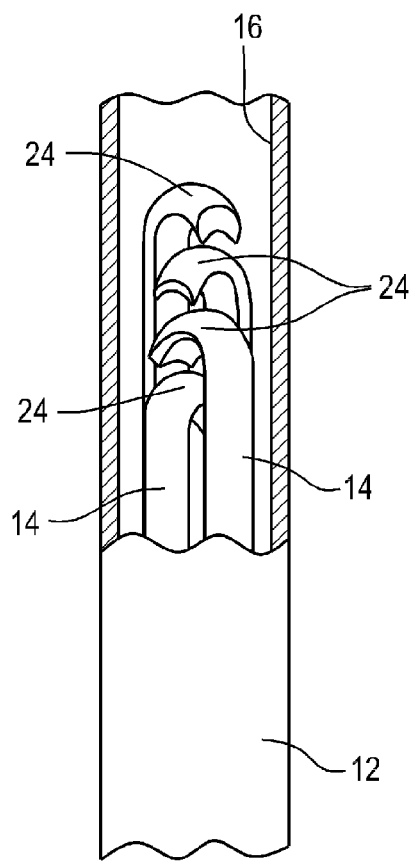
FIGS. 7 and 8 are end and cross-sectional views, respectively, showing the extraction device of FIG. 2 in a stowed position thereof.
Figure 7:
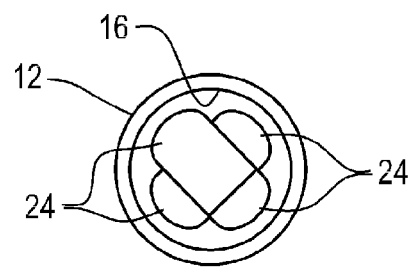

The distal portions 20 of the legs 14 are represented in FIGS. 1 and 2 as being substantially straight (rectilinear). The distal portion 20 of each leg 14 is defined by a limited length of its leg 14 and pivots relative to the remainder of its leg. The distal portion 20 of each leg 14 preferably pivots in a manner that creates a uniform radius 22 that serves as a transition between the straight distal portion 20 of the leg 14 and the straight remainder of the leg 14 within the sheath 12. The legs 14 of the devices 10 and 50 are preferably formed from a sufficiently rigid material, such as a stainless steel or a "shape memory" nickel-titanium alloy such as NITINOL, so that the distal portions 20 of the legs 14 automatically deploy radially outward and away from each other when the legs 14 are deployed outside the sheath 12. As a result, the devices 10 and 50 do not require a plunger capable of being actuated relative to the legs 14 in order to force the legs 14 radially apart as seen in FIGS. 1 and 2. The legs 14 are sufficiently elastically deformable so that, when the sheath is advanced over them, the legs 14 elastically collapse radially toward each other to acquire a stowed position shown in FIGS. 5 through 8, in which the legs 14 are largely stowed within the sheath 12, substantially straight along a longitudinal axis thereof, and substantially parallel to each other, as depicted in FIGS. 6 and 8.

Figure 3:
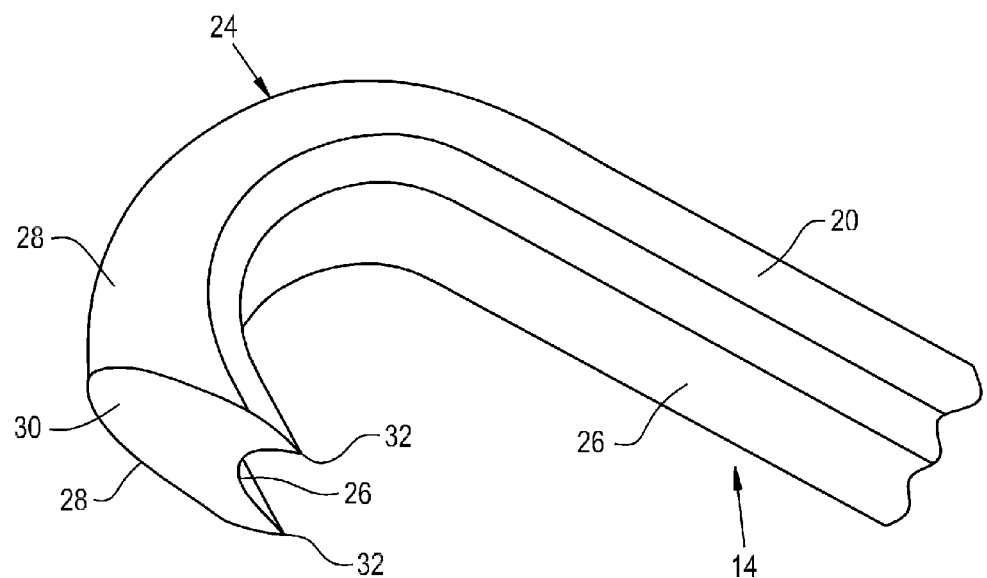
FIG. 3 is a perspective view of a distal end of a leg of either extraction device of FIGS. 1 and 2.

FIG. 3 shows the distal end 24 of one of the legs 14 of FIG. 1 or 2. As represented in FIG. 3, each leg 14 has a concave-convex cross-sectional shape that contributes greater strength to the legs 14, such that the legs 14 maintain their form and alignment and provide greater grasping strength and expansion force than extraction devices 10 and 50 equipped with wires having other cross-sectional shapes. As a result, the devices 10 and 50 are well suited for moving, manipulating and extracting biological material, such as calculi, stones, etc. As depicted in FIG. 3, the cross-section of each leg 14 is concave-convex in the sense that the inward surfaces 26 of the legs 14 that face each other are concave, while the oppositely-disposed outward surfaces 28 of the legs 14 are convex. The cross-sectional shape of the legs 14 can be produced by various processes, such as stamping, rolling, extruding, etc.

A key feature of the present invention is that the distal end 24 of each leg 14 is arcuate, following an arc of greater than 90 degrees, for example, between about 135 and 180 degrees. Furthermore, the distal end 24 of each leg 14 defines a distal surface 30 that is substantially flat and parallel to the longitudinal axis of its corresponding leg 14 when the leg 14 is in its stowed position. Finally, the concave inward surface 26 of each leg 14 (the surface facing the other legs 14 of the device10 or 50) defines a pair of points 32 with the corresponding distal surface 30 of its leg 14. While two points 32 are shown, it is foreseeable that the distal surface 30 or the cross-section of the legs 14 could be modified to create more than two points 32. The multi-point configuration at the distal ends 24 of the legs 14 defines what may be referred to as a claw, which promotes the ability of the devices 10 and 50 to grasp and hold a variety of biological materials. As evident from FIGS. 5 through 8, the distal ends 24 of the legs 14 have staggered lengths so that when the legs 14 are fully collapsed and stowed with the sheath 12, their arcuate portions and distal surfaces 30 do not interfere with each other.

Figure 4:
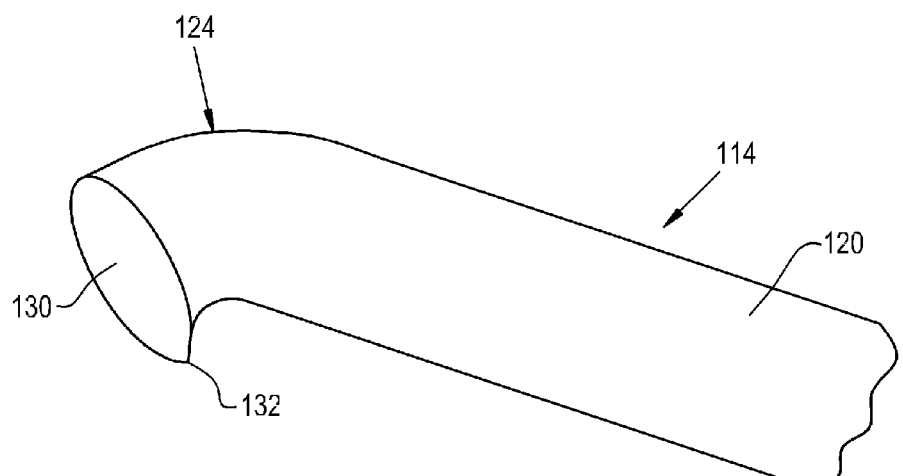
FIG. 4 is a perspective view of a distal end of a leg of a prior art extraction device.
Figure 5:
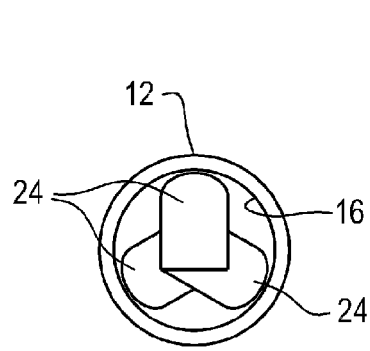
FIGS. 5 and 6 are end and cross-sectional views, respectively, showing the extraction device of FIG. 1 in a stowed position thereof.

For comparison, FIG. 4 shows a distal end 124 of a conventional leg 114 for an extraction device known in the prior art. While the distal end 124 of the leg 114 is arcuate, it follows an arc of less than 90 degrees. Furthermore, the distal end 124 of the leg 114 defines a distal surface 130 that is not parallel to the longitudinal axis of the leg 114. Finally, the leg 114 has a circular cross-sectional shape, and with the distal surface 130 defines a single point 132.

The multi-point configuration of the legs 14 shown in FIGS. 1-3 and 5-8 provide various advantages. One such advantage is that the curvature of their distal ends 24, which may be defined by a substantially constant outer radius, is greater than ninety degrees, which greatly reduces the risk that the legs 14 may cause an unintended perforation. Furthermore, the shape of the distal ends 24 yields multiple grasping points 32 per leg 14. In the three-leg 14 embodiment of FIGS. 1, 5 and 6, six grasping points 32 are defined, and in the four-leg 14 embodiment of FIGS. 2, 7 and 8, eight grasping points 32 are defined. The multiple grasping points 32 greatly increase the grasping effect on a biological material, such as a stone (calculi), and promote the ability of the extraction devices 10 and 50 of FIGS. 1 and 2 to hold a biological material in a fixed position during the laser disintegration process. In urological and gynecological procedures, stones (calculi) tend to migrate up into the kidney due to the impact of the laser energy against the stone. This undesirable migration, known as "retropulsion," can be minimized with the arcuate distal legs 14 depicted in FIGS. 1-3 and 5-8.

The arcuate shape of the distal ends 24 of the legs 14 is also beneficial when the device 10 or 50 is configured or otherwise used as a simple grasper/extraction device, in which case "lasing" of a stone (calculi) or other biological material is not necessary. In this scenario, the superior grasping effect of the multi-point claws enhances the ability of the device 10 or 50 to grasp and extract biological material through an existing body orifice. The elastically deformable legs 14 enable their distal ends 24 to also release a biological material by advancing the sheath 12 over the legs 14, enabling a user to release a biological material (for example, a stone/calculi) that is too large to pass out of the body through a natural orifice.

Another feature of the legs 14 is that their concave inner surfaces 26 cooperate to define a central channel, through which the laser fiber 18(for example, a diameter of 145 micrometers or more) can be passed to disintegrate calculi, blood clots, kidney stones, bladder stones, biliary tract stones, gall stones, and other solid human or animal calculi. The devices 10 and 50 enable a user to lase or break up stones (calculi) or other biological material into multiple pieces and immediately use the distal ends 24 as forceps to grasp, manipulate and remove the individual pieces without inserting another device, until the patient is stone-free. The legs 14 are preferably sufficiently resilient so that they are able to securely grasp biological material, without the need for a basket to fully enclose the material. This aspect provides another safety feature by eliminating a basket tip that could be inadvertently cut off by the laser and left in the body during the lasing process.

As evident from FIGS. 5-8, another feature of the invention is that benefits of the "clawed" legs 14 is their ability to collapse into their stowed positions such that the claws are in a juxtapositioned configuration, whereby their distal ends 24 are axially (longitudinally) and angularly spaced from each other such that a minimal collapsed outside diameter can be acquired.

The devices 10 and 50 represented in FIGS. 1-3 and 5-8 can be used in essentially any medical field (human or veterinary), that utilizes an endoscope, such as (but not limited to) urology, gynecology, gastroenterology, arthroscopy, cardiology (cardio-vascular), and general surgery.

While the invention has been described in terms of a preferred embodiment, it is apparent that other forms could be adopted by one skilled in the art. For example, appropriate materials could be substituted for those noted. Accordingly, the scope of the invention is to be limited only by the following claims.

The invention claimed is:

1. An extraction device having a sheath with an interior passage and legs slidably received within the passage of the sheath, the legs being adapted to move outwardly away from each other when deployed from the sheath to establish a deployed position, and to move inwardly toward each other to collapse within the sheath and define a stowed position, each of the legs having a centerline, a distal portion encompassing a longitudinal portion of the centerline, a distal end encompassing a second portion of the centerline and having an arcuate portion that extends from the distal portion along an arc of greater than 90 degrees to a distal surface thereof that is intersected by the second portion of the centerline, and a concave-convex cross-sectional shape transverse to the centerline and defined by and between a first surface that is concave and present on the distal portion and the distal end and an oppositely-disposed second surface that is convex and present on the distal portion and the distal end, the legs being oriented by the passage of the sheath such that the first surfaces thereof face each other, each of the distal surfaces being oriented transverse to and between the first and second surfaces of the distal end thereof and at an oblique angle to the second portion of the centerline of the distal end thereof where the second portion of the centerline intersects the distal surface such that the distal surfaces of the legs face each other, the distal surface of each of the distal ends defining a grasping and holding feature with the first surface of the corresponding leg, each grasping and holding feature comprising at least two extremities that define at least first and second points that project farther toward the sheath than any other region of the distal surface and are adapted for grasping when the legs are retracted into the sheath, the first point being defined by a first intersection of the first, second, and distal surfaces of the corresponding leg, the second point being defined by a second intersection of the first, second, and distal surfaces of the corresponding leg.

2. The extraction device according to claim 1, wherein when fully collapsed the legs define a tubular shape having a central channel defined by the first surfaces of the legs.

3. The extraction device according to claim 1, wherein each of the distal surfaces is parallel to the longitudinal portion of the centerline of the corresponding distal portion thereof.

4. The extraction device according to claim 1, wherein the device has more than two of the legs and the first surfaces of the legs face each other.

5. The extraction device according to claim 1, wherein the device is a forceps chosen from the group consisting of urological, gynecological, cardiological, laparoscopical and gastro-intestinal instruments.

6. The extraction device according to claim 1, wherein the arc along which the arcuate portion of each of the distal ends extends is between 135 to 180 degrees and the distal surface of each of the distal ends is parallel to the longitudinal portion of the centerline of the corresponding distal portion thereof.

7. The extraction device according to claim 1, wherein the first and second points of each of the distal ends are separated by the first surface of the corresponding leg.

8. The extraction device according to claim 1, the arc along which the arcuate portion of each of the distal ends extends is between 135 to 180 degrees.

9. The extraction device according to claim 1, wherein the distal ends are adjacent each other when the legs are in the stowed position.

10. The extraction device according to claim 9, wherein the distal ends of the legs have staggered lengths so that when the legs are collapsed and stowed with the sheath, the arcuate portions and the distal surfaces of the legs are axially spaced apart from each other.

11. The extraction device according to claim 1, wherein each of the distal portions of the legs is pivotably connected to a rectilinear second portion of the corresponding leg by a uniform radius that serves as a transition between the distal and second portions of the corresponding leg.

12. A method of using the extraction device of claim 1, the method comprising:
deploying the distal portions of the legs from the sheath within a patient;
grasping a biological material with the first and second points; and
holding the biological material in a fixed position during laser disintegration of the biological material.

13. The method of claim 12, wherein the method is a urological or gynecological procedure and the biological material is calculus.

14. The method of claim 12, wherein the biological material is chosen from the group consisting of calculi, blood clots, kidney stones, bladder stones, biliary tract stones, and gall stones.

15. The method of claim 12, wherein the biological material is broken into multiple pieces, the method further comprising using the distal ends of the legs to grasp, manipulate and remove the individual pieces from the patient.

16. A method of using the extraction device of claim 1, the method comprising:
deploying the distal portions of the legs from the sheath within a patient;
grasping a biological material with the first and second points; and
extracting the biological material through a body orifice of the patient.

17. The method of claim 16, wherein the method is a urological or gynecological procedure and the biological material is calculus.

18. The method of claim 16, wherein the biological material is chosen from the group consisting of calculi, blood clots, kidney stones, bladder stones, biliary tract stones, and gall stones.

19. A surgical instrument chosen from the group consisting of urological, gynecological, cardiological, laparoscopical and gastro-intestinal forceps, the surgical instrument comprising:
a sheath having an interior passage;
legs slidably received within the passage of the sheath, the legs being adapted to move outwardly away from each other when deployed from the sheath to establish a deployed position, and to move inwardly toward each other to collapse within the sheath and define a stowed position;
each of the legs having a centerline, a first portion, a distal portion pivotally connected to the first portion and encompassing a longitudinal portion of the centerline, a distal end that encompasses a second portion of the centerline and is continuously arcuate from the distal portion of the corresponding leg along an arc of greater than 90 degrees to a distal surface thereof that is intersected by the second portion of the centerline, and a concave-convex cross-sectional shape transverse to the centerline and defined by and between a concave surface and an oppositely-disposed convex surface that are present on the distal portion and the distal end, the legs being oriented by the passage of the sheath such that the concave surfaces thereof face each other; and each of the distal surfaces being oriented transverse to and between the concave and convex surfaces of the distal end thereof, at an oblique angle to the second portion of the centerline of the distal end thereof where the second portion of the centerline intersects the distal surface such that the distal surfaces of the legs face each other, and parallel to the centerline of the corresponding distal portion thereof, the distal surface of each of the distal ends being parallel to the centerline of the corresponding distal portion thereof, each of the distal ends having at least two extremities that define at least first and second points adapted for grasping when the legs are retracted into the sheath, the first point being defined by a first intersection of the concave, convex, and distal surfaces of the corresponding leg, the second point being defined by a second intersection of the concave, convex, and distal surfaces of the corresponding leg, the first and second points of each of the distal ends being separated by the concave surface of the corresponding leg and projecting farther toward the sheath than any other region of the distal surface thereof.

20. The extraction device according to claim 19, wherein the distal ends of the legs have staggered lengths so that when the legs are collapsed and stowed with the sheath, the arcuate portions and the distal surfaces of the legs are axially spaced apart from each other.

\* \* \* \* \*